US011946932B2

(12) United States Patent
Chen

(10) Patent No.: US 11,946,932 B2
(45) Date of Patent: Apr. 2, 2024

(54) INTEGRATED MICROFLUIDIC SYSTEM FOR AUTOMATED MULTIPLEX ANALYTE DETECTION

(71) Applicant: WellSIM Biomedical Technologies, Inc., San Jose, CA (US)

(72) Inventor: Yuchao Chen, Rodeo, CA (US)

(73) Assignee: WellSIM Biomedical Technologies, Inc., San Jose, CA (US)

( * ) Notice: Subject to any disclaimer, the term of this patent is extended or adjusted under 35 U.S.C. 154(b) by 0 days.

(21) Appl. No.: 18/326,021

(22) Filed: May 31, 2023

(65) Prior Publication Data

US 2023/0384303 A1      Nov. 30, 2023

Related U.S. Application Data

(60) Provisional application No. 63/347,549, filed on May 31, 2022.

(51) Int. Cl.
*G01N 33/543* (2006.01)
*B01L 3/00* (2006.01)
*G01N 33/68* (2006.01)

(52) U.S. Cl.
CPC .. *G01N 33/54386* (2013.01); *B01L 3/502761* (2013.01); *G01N 33/6896* (2013.01); *B01L 2200/0647* (2013.01); *B01L 2200/16* (2013.01); *B01L 2300/0654* (2013.01);
(Continued)

(58) Field of Classification Search
CPC ......... G01N 33/54386; G01N 33/6896; G01N 2333/4709; G01N 2800/2821; B01L 3/502761; B01L 2200/0647; B01L 2200/16; B01L 2300/0654; B01L 2400/0487
See application file for complete search history.

(56) References Cited

U.S. PATENT DOCUMENTS

2012/0177543 A1* 7/2012 Battrell ................. F04B 43/043
 422/187
2013/0089874 A1* 4/2013 Manger ............... F16K 99/0026
 435/6.15
(Continued)

*Primary Examiner* — Christine T Mui
*Assistant Examiner* — Jonathan Bortoli
(74) *Attorney, Agent, or Firm* — Jun He Law Offices P.C; Yi Zhang

(57) ABSTRACT

The present disclosure provides an automatic and portable system, comprising a bench-top instrument and a disposable microfluidic device for multiplex detection and quantitation of biomolecules such as proteins and nucleic acids from biological samples. The disposable device pre-encapsulates all the reagents including capture probes, detection probes, and wash buffer, with a waste reservoir in it, allowing all the liquids to be circulated inside the device, without interaction with the external environment. The bench-top instrument comprises a pressure control module and a fluorescence detection module, enabling automatic device operation and signal detection without manual intervention. This system with the advantages of automation, portability, high speed, high sensitivity, low sample consumption, low cost, multiplex detection, and high versatility, can be applied to rapid on-site biomolecule detection, such as virus detection, analysis of extracellular vesicle surface markers, and quantification of antigens, antibodies, and gene expression.

23 Claims, 9 Drawing Sheets

(52) U.S. Cl.
CPC ............... *B01L 2400/0487* (2013.01); *G01N 2333/4709* (2013.01); *G01N 2800/2821* (2013.01)

(56) References Cited

U.S. PATENT DOCUMENTS

| | | | |
|---|---|---|---|
| 2014/0295415 A1* | 10/2014 | Rolland | C12Q 1/68 435/6.1 |
| 2015/0083313 A1* | 3/2015 | Putnam | B32B 38/0004 156/60 |
| 2020/0070168 A1* | 3/2020 | Reategui | B01F 25/4317 |

* cited by examiner

INTEGRATED MICROFLUIDIC SYSTEM FOR AUTOMATED MULTIPLEX ANALYTE DETECTION

CROSS-REFERENCE TO RELATED APPLICATIONS

This application claims the priority of U.S. provisional application 63/347,549, filed May 31, 2022, the entire disclosure of which are incorporated herein by reference.

FIELD OF THE INVENTION

The present invention generally relates to integrated microfluidic system. More particularly, the invention relates to a system for detecting disease related biomarker using microfluidic device in combine with enzyme-linked immunoassay (ELISA) and microarray technologies.

BACKGROUND OF THE INVENTION

Enzyme-linked immunoassay (ELISA) and microarray technologies have been applied to the detection of various biomolecular, such as proteins and nucleic acids with the advantages of high throughput and high sensitivity. However, due to their labor-intensive procedures and lack of integrated device and system, these approaches are usually limited for laboratory use and have not yet been applied to point-of-care tests (POCT).

To address these challenges, this invention presents an integrated microfluidic system, including a monolithic disposable microfluidic device with reagents, a pressure-control module, and a detection module, for fully automated device operation and biomolecular detection. With the advantages of multiplex detection, fully automation, portability, low cost, and high sensitivity, this platform could be utilized for on-site biological sample analysis, such as virus detection, analysis of extracellular vesicle surface markers, and quantification of antigens and gene expression.

BRIEF SUMMARY OF THE INVENTION

The present disclosure provides an automatic and portable system, comprising a bench-top instrument and a disposable microfluidic device for multiplex detection and quantitation of biomolecules such as proteins and nucleic acids from biological samples. The disposable device pre-encapsulates all the reagents including capture probes, detection probes, and wash buffer, with a waste reservoir in it, allowing all the liquids to be circulated inside the device, without interaction with the external environment. The bench-top instrument comprises a pressure control module and a fluorescence detection module, enabling automatic device operation and signal detection without manual intervention. This system with the advantages of automation, portability, high speed, high sensitivity, low sample consumption, low cost, multiplex detection, and high versatility, can be applied to rapid on-site biomolecule detection, such as virus detection, analysis of extracellular vesicle surface markers, and quantification of antigens, antibodies, and gene expression.

In one aspect, the present disclosure provides a microfluidic device comprising:
(a) a reagent layer,
(b) a microfluidic layer beneath the reagent layer, and
(c) a substrate layer beneath the microfluidic layer.

In some embodiments, the reagent layer comprises a sample reservoir for loading a sample solution, a washing buffer reservoir for depositing a washing buffer solution, a detection probe reservoir for depositing a detection probe solution, and a waste reservoir for collecting waste.

In some embodiments, the microfluidic layer comprises a sample zone for receiving liquid from the sample reservoir, a washing buffer zone for receiving liquid from the washing buffer reservoir, a detection probe zone for receiving liquid from the detection probe reservoir, and at least one reaction zone.

In some embodiments, the reaction zone is connected with and allow the inflow of the liquid from the sample zone, the liquid from the washing buffer zone and the liquid from the detection probe zone. In some embodiment, the reaction zone is connected with and allow the outflow of liquid from the reaction zone to the waste reservoir.

In some embodiments, the waste reservoir further comprises a vacuum access channel.

In some embodiments, the vacuum access channel is connected to a vacuum unit for microfluidic control.

In some embodiments, the microfluidic device further comprising a pierceable isolation layer spaced between the reagent layer and the microfluidic layer.

In some embodiments, the pierceable isolation layer block the liquid flow from the sample reservoir, the washing buffer reservoir, and the detection probe reservoir to the sample zone, the washing buffer zone, and the detection probe zone, respectively.

In some embodiments, the pierceable isolation layer can be pierced to allow the liquid flow from the sample reservoir, the washing buffer reservoir, and the detection probe reservoir to the sample zone, the washing buffer zone, and the detection probe zone, respectively.

In some embodiments, the pierceable isolation layer is adhesive.

In some embodiments, the liquid from the sample zone, the washing buffer zone and the detection probe zone flows to the reaction zone independently through individual channels.

In some embodiments, the sample zone, the washing buffer zone and the detection probe zone are interconnected and the liquid from the sample zone, the washing buffer zone and the detection probe zone can flow to the reaction zone in any sequence.

In some embodiments, the microfluidic device further comprises an adhesive layer spaced between the microfluidic layer and the substrate layer.

In some embodiments, the adhesive layer does not block the liquid flow within the microfluidic device.

In some embodiments, the substrate layer is a glass substrate.

In some embodiments, the substrate layer is immobilized with an analyte-capturing agent to form a modified surface.

In some embodiments, the modified surface in the substrate layer and the reaction zone in the microfluidic layer jointly form a reaction chamber.

In some embodiments, the sample solution and the detection probe solution are mixed in, or successively pass through the reaction chamber to produce a detectable signal.

In some embodiments, the analyte-capturing agent is a capture antibody.

In some embodiments, the capture antibody is a capture antibody is an antibody against to an antigen, wherein the antigen is selected form the group consisting of t-tau, p-tau181, p-tau217, p-tau231, NMDAR2A, Aβ40, Aβ42, CD9, CD18, CD63, CD81, CD56, and CD171.

In another aspect, the present disclosure provides a microfluidic detection system comprising: (a) a microfluidic device described herein; (b) a pressure control module; and (c) a signal detection module.

In some embodiments, the pressure control module comprises: (a) a vacuum unit providing negative pressure; (b) valves controlling the pressure within the sample reservoir, washing buffer reservoir, and detection probe reservoir; wherein negative pressure drives the liquid flow within the microfluidic device.

In some embodiments, the vacuum unit is connected to a vacuum access channel in the waste reservoir of the microfluidic device.

In some embodiments, the pressure control module further comprises a puncture unit which can puncture the pierceable isolation layer.

In some embodiments, the puncture unit is integrated into the valve.

In some embodiments, the puncture unit is integrated into the valve.

In some embodiments, the microfluidic detection system further comprises a sealing layer between the microfluidic device and the pressure control module.

In some embodiments, the signal detection module detects an optical signal.

In some embodiments, the signal detection module detects fluorescence.

In some embodiments, the signal detection module is a laser-induced confocal fluorescence scanner or a fluorescence microscope.

In another aspect, the present disclosure provides a method for using the microfluidic device described herein for detection, which comprises the following steps:
(1) driving the sample solution in the sample reservoir 11 flowing into the reaction zone 34;
(2) driving the detection probe solution in the detection probe reservoir 13 flowing into the reaction zone 34;
(3) allowing the sample solution and the detection probe solution to be mixed in, or to be successively pass through the reaction zone 34 to produce a detectable signal.

In another aspect, the present disclosure provides a method for using the microfluidic device described herein for detection, which comprises the following steps:
(1) puncturing the pierceable isolation layer between the sample zone and the sample reservoir, and allowing the sample solution to flow into the reaction zone,
(2) puncturing the pierceable isolation layer between the detection probe zone and the detection probe reservoir, and allowing the detection probe solution to flow into the reaction zone,
(3) allowing the sample solution and the detection probe solution to be mixed in, or to be successively pass through the reaction zone to produce a detectable signal.

In some embodiments, the method further comprises a detection step, comprising detecting the signal produced in the reaction step by a signal detection module.

In some embodiments, the method further comprising a washing step, comprising puncturing the pierceable isolation layer between the washing buffer zone and the washing buffer reservoir, and allowing the washing buffer solution to flow into the reaction zone.

In some embodiments, the sample solution comprises a circulating extracellular vesicle (EV).

In some embodiments, the analyte-capturing agent is a capture antibody against a disease-specific antigen present on the surface of the circulating EV.

In some embodiments, the detection probe is a detection antibody with a detectable label.

In some embodiments, the detection antibody is an antibody against a disease-specific antigen present on the surface of the circulating EV.

In some embodiments, the disease-specific antigen is selected from the group consisting of t-tau, p-tau181, p-tau217, p-tau231, Aβ40, and Aβ42.

In some embodiments, the sample is from a subject suspected to have Alzheimer's disease (AD).

In some embodiments, the detectable label is a fluorophore or a fluorescent microsphere.

In some embodiments, the detectable label is detected through the signal detection module.

In some embodiments, the signal detection module is a laser-induced confocal fluorescence scanner or a fluorescence microscope.

These and other features, aspects, and advantages of the present invention will become better understood with regard to the following description, appended claims and accompanying drawings.

BRIEF DESCRIPTION OF THE FIGURES

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION OF THE INVENTION

Figure 1:
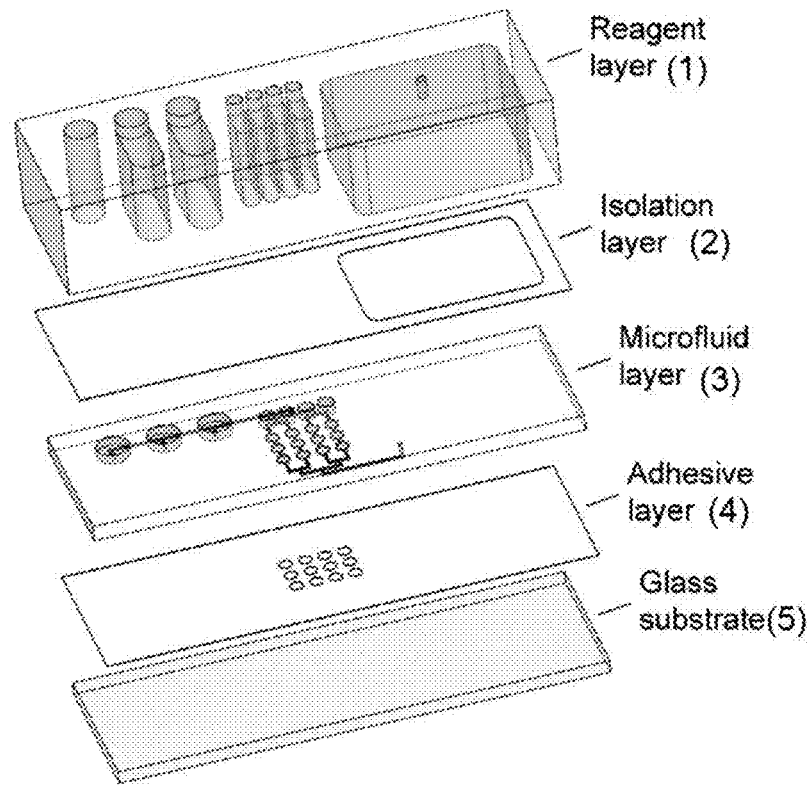
FIG. 1 shows the design of a disposable microfluidic device for multiplex analyte detection. The device comprises of five layers, including a reagent layer, an isolation layer, a microfluid layer, an adhesive layer, and a glass substrate from top to bottom, respectively.

In the Summary of the Invention above and in the Detailed Description of the Invention, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or particular claim, that feature can also be used, to the extent possible, in combination with and/or in the context of other particular aspects and embodiments of the invention.

Throughout the present disclosure, the articles "a," "an," and "the" are used herein to refer to one or to more than one (i.e., to at least one) of the grammatical object of the article. By way of example, "a compound" means one compound or more than one compound.

As used herein, the term "and/or" indicates that one or more of the stated cases may occur, alone or in combination with at least one of the stated cases, up to with all of the stated cases, and in the invention generally.

The term "comprise" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Where a range of value is provided, it is understood that each intervening value, to the tenth of the unit of the lower limit unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, the embodiments described herein can be practiced without there specific details. In other instances, methods, procedures and components have not been described in detail so as not to obscure the related relevant function being described. Also, the description is not to be considered as limiting the scope of the implementations described herein. It will be understood that descriptions and characterizations of the embodiments set forth in this disclosure are not to be considered as mutually exclusive, unless otherwise noted.

Overall Microfluidic Device Layout

In one aspect, the present disclose provides a microfluidic device.

An exemplary embodiment of the microfluidic device described herein is illustrated in FIG. 1. Referring to FIG. 1, the microfluidic device is composed of a reagent layer 1, a microfluidic layer 3 beneath the reagent layer 1, and a substrate layer 5 beneath the reagent microfluidic layer 3.

In some embodiments, the microfluidic device further comprises a pierceable isolation layer 2 spaced between the reagent layer 1 and the microfluidic layer 3, and an adhesive layer 4 spaced between the microfluidic layer 3 and the substrate layer 5.

The methods of manufacturing the microfluidic device disclosed herein are known in the art (see, e.g., Scott, S. M. and Ali, Z., Fabrication Methods for Microfluidic Devices: An Overview, Micromachines, 2021, 12, 319). In some embodiments, the reagent layer and microfluid layer are made of plastic polymer such as PMMA and PC and fabricated by CNC milling, hot embossing, 3D printing, or injection molding. The isolation layer and adhesive layer are made of plastic membrane, such as acrylic membrane, with adhesive on it for assembly.

To encapsulates all the reagents with microfluidic device for automated operation with minimum manual intervention, the reagent layer 1 comprises several reservoirs for loading sample solution, and depositing washing buffer solutions and detection probe solutions.

The microfluidic layer 3 comprises several zones to receive the liquid flow from reservoirs and reaction zones to detect the analyte in sample solution.

The number of reservoirs/zones can be adjusted in according to the specific need. For example, when more than one sample is to be tested, more than one sample reservoirs/zones can be set in the device. Similar, the number of washing buffer reservoirs/zones can be adjusted according to the number of washing steps; The number of detection probe reservoirs/zones can be adjusted according to the makers of interest.

The substrate layer 5 is immobilized with analyte-capturing agents to capture the analyte in the sample solution.

The pierceable isolation layer 2 is placed under the reagent layer 1 and preserve the solution within the reservoirs before the detection starts.

The pierceable isolation layer 2 and the adhesive layer 4 facilitate the assembling of the microfluidic device.

The Reagent Layer

In the reagent layer, there are different reservoirs to store sample (e.g., plasma, urine, and saliva), wash buffers (e.g., PBS, PSBT, SSC, and TE buffer), and detection probes (e.g., fluorescently labeled antibodies and oligonucleotides).

The wash buffers and detection probes are encapsulated inside the reservoirs by the isolation layer in advance. Furthermore, there is a waste reservoir to collect the used reagents without interact with external environment.

Figure 2:
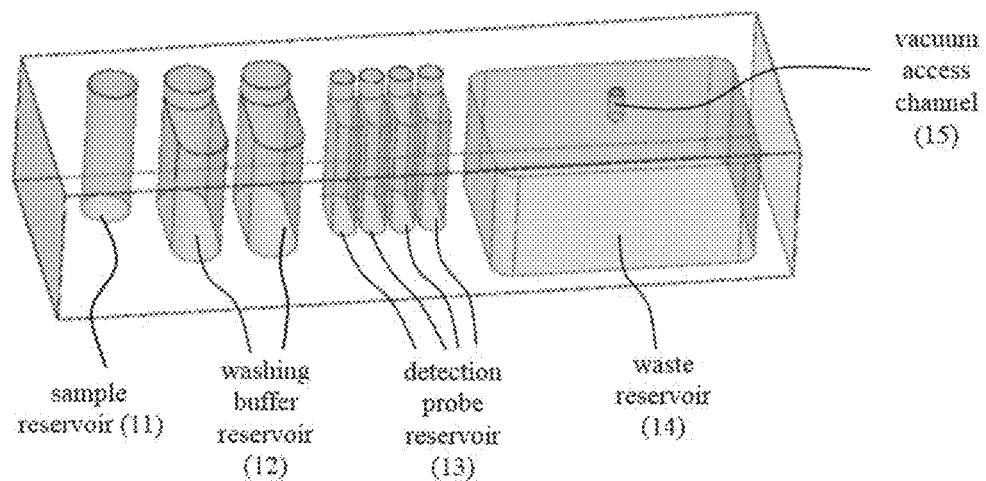
FIG. 2 shows a reagent layer of the microfluidic device according to an embodiment of the invention.

As shown in FIG. 2, the reagent layer 1, comprising a sample reservoir 11 for loading a sample solution, a washing buffer reservoir 12 for depositing a washing buffer solution, a detection probe reservoir 13 for depositing a detection probe solution, and a waste reservoir 14 for collecting waste.

The reservoirs are open on the top for connecting a valve, a vacuum pump, or a syringe pump. In some embodiments, the waste reservoir 14 further comprises a vacuum access channel 15.

The sample reservoir 11, washing buffer reservoir 12 and detection probe reservoir 13 are open on the bottom enabling the liquids in reservoirs flowing downwards to the microfluidic layer 3 for reaction and detection.

The waste reservoir 14 is open on the bottom for receiving the waste.

In some embodiments, the waste reservoir further comprises a vacuum access channel 15.

The number of reservoirs can be adjusted according to different detection needs.

Microfluidic Layer

The microfluidic layer 3 comprising a sample zone 31 for receiving liquid from the sample reservoir 11, a washing buffer zone 32 for receiving liquid from washing buffer reservoir 12, detection probe zone 33 for receiving liquid from detection probe reservoir 13.

Figure 3:
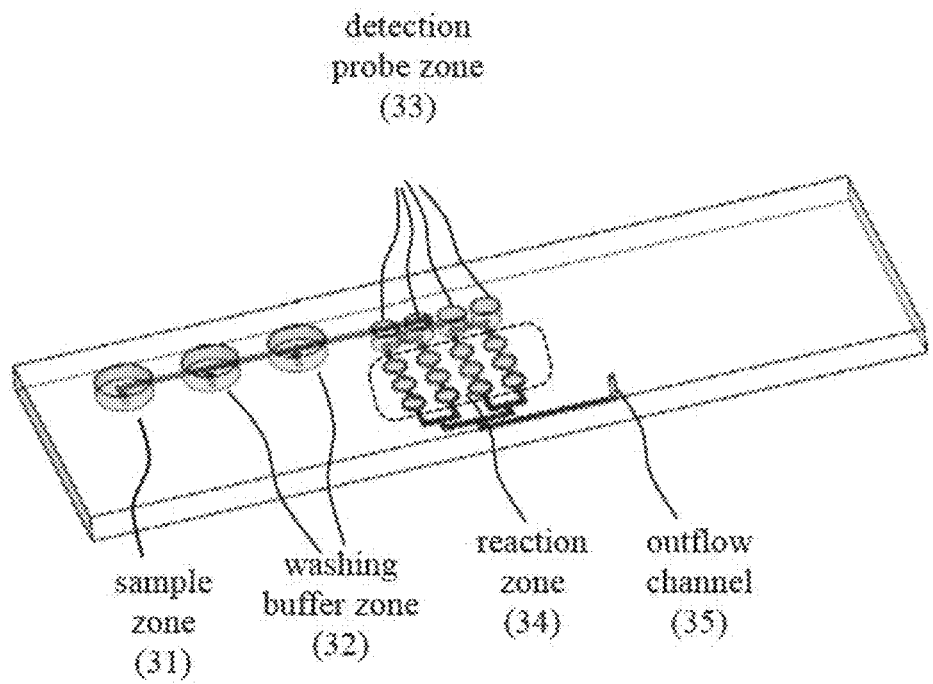
FIG. 3 shows a microfluidic layer of the microfluidic device according to an embodiment of the invention.

As shown in FIG. 3, the sample zone 31, washing buffer zone 32, and detection probe zone 33 are open on the top for receiving liquid. The bottoms of sample reservoir 11, washing buffer reservoir 12 and detection probe reservoir 13 are aligned with the tops of sample zone 31, washing buffer zone 32, and detection probe zone 33 respectively, as shown in the figure.

Figure 4:
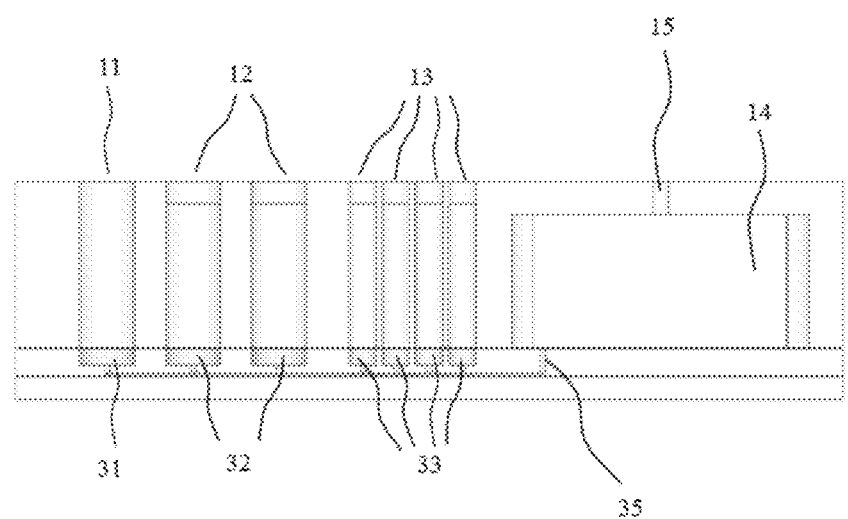
FIG. 4 shows the design after assembly.

As shown in FIG. 4, the side view of the microfluidic device, for the need of detection, plurality of sample zone, washing buffer zone and detection probe zone can be set according to the number of corresponding reservoirs.

The reaction zone 34 is in communication with and allow the inflow of the liquid from the sample zone 31, the washing buffer zone 32 and the detection probe zone 33. Under driving forces, for example, negative pressure, liquid in sample zone 31, washing buffer zone 32 and detection probe zone 33 can flow into reaction zone 34. The waste will flow out of reaction zone 34 and flow into waste reservoir 14 through an outflow channel 35.

In some embodiments, the liquid from the sample zone 31, the washing buffer zone 32 and the detection probe zone 33 flow to the reaction zone 34 independently through individual channels. In some embodiments, the liquid from the sample zone 31, the washing buffer zone 32 and the detection probe zone 33 flow to the reaction zone 34 through one channel.

In some embodiments, the liquid from the sample zone 31, the washing buffer zone 32 and the detection probe zone 33 are interconnected and the liquid from the sample zone 31, the washing buffer zone 32 and the detection probe zone 33 can flow to the reaction zone 34 in any sequence.

Figure 5:
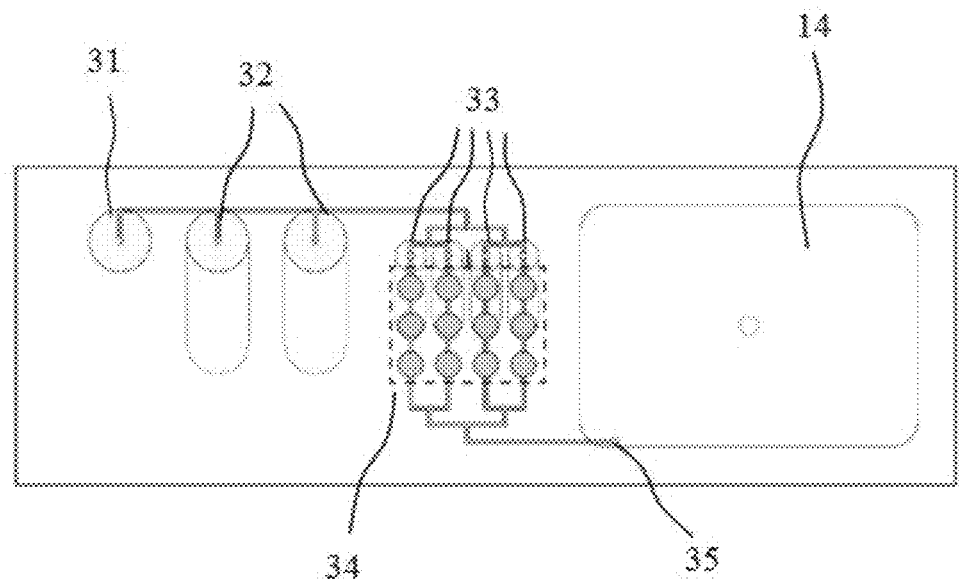
FIG. 5 shows the bottom view of the assembled microfluidic device.

FIG. 5 shows the bottom view of the assembled microfluidic device. On the microfluidic layer, there is an array of reaction zones 34, with capture probes labeled on the glass substrate and can be used to detect 4 different combinations of targeting molecules with 3 replications for each. With this design, all the sample and reagents pass through the detection region and eventually go into the waste reservoir 14 under the driven of a negative pressure.

Multiple reaction zones can be arranged on single liquid flowing path to achieve the purpose of repeating experiments and reducing errors. Replication can be three or more, according to the needs of detection.

Multiple detection probe zone can be arranged on single liquid flowing path to achieve an assay requiring multiple detection reagents. For example, a classic ELISA requires a primary antibody and a labeled second antibody attached, in which case two detection probes are needed.

Variations of these designs can be adjusted by those skilled in the art according to this disclosure and the specific need, and are included in the present invention without the limitation of the layout shown in the figure.

The Isolation Layer

The pierceable isolation layer 2 is spaced between the reagent layer 1 and the microfluidic layer 3.

Before the test, the pierceable isolation layer plays a role in blocking the flow of liquid to preserve the liquid. The pierceable isolation layer can block the liquid flow from the sample reservoir 11, the washing buffer reservoir 12, and the detection probe reservoir 13 to the sample zone 31, the washing buffer zone 32, and the detection probe zone 33, respectively.

Figure 6:
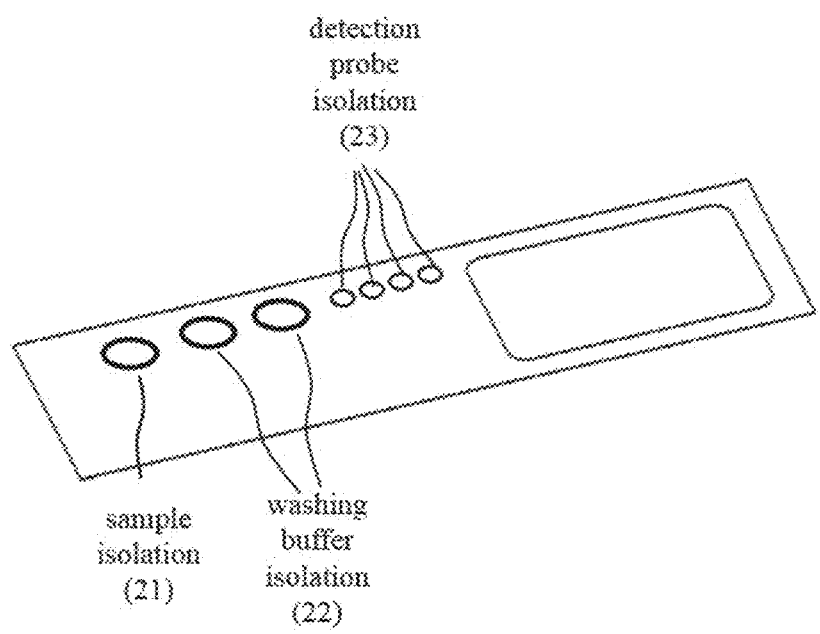
FIG. 6 shows a pierceable isolation layer of the microfluidic device according to an embodiment of the invention.

Specifically, as shown in the FIG. 6, the sample isolation 21, the washing buffer isolation 22, and the detection probe isolation 23 are pierceable. The puncture of the sample isolation 21, the washing buffer isolation 22, and the detection probe isolation 23 allow the liquid flow from the sample reservoir, the washing buffer reservoir, and the detection probe reservoir to the sample zone 31, the washing buffer zone 32, and the detection probe zone 33, respectively.

The pierceable isolation layer can be adhesive for use in the assembling of the microfluidic device.

The Substrate Layer

The substrate layer 5 is a substrate with flat surface. In some embodiments, the substrate layer 5 is a glass substrate.

In some embodiments, the sample solution and the detection probe solution are mixed in, or successively pass through the reaction chamber to produce a detectable signal.

In some embodiments, the substrate layer is immobilized with an analyte-capturing agent to form a modified surface. The analyte-capturing agent can be a small molecule compound, a polypeptide or a nucleic acid. In some embodiments, the analyte-capturing agent is an aptamer. In some embodiments, the analyte-capturing agent is a capture antibody.

In some embodiments, the capture antibody is a capture antibody is an antibody against to an antigen, wherein the antigen is selected form the group consisting of t-tau, p-tau181, p-tau217, Aβ40, Aβ42, CD9, CD18, CD63, CD81, CD56, and CD171.

In some embodiments, the modified surface in the substrate layer 5 and the reaction zone 34 in the microfluidic layer jointly form a reaction chamber. In some embodiment, only the surface under the reaction zone 34 is modified.

The Reaction Chamber

Figure 7:
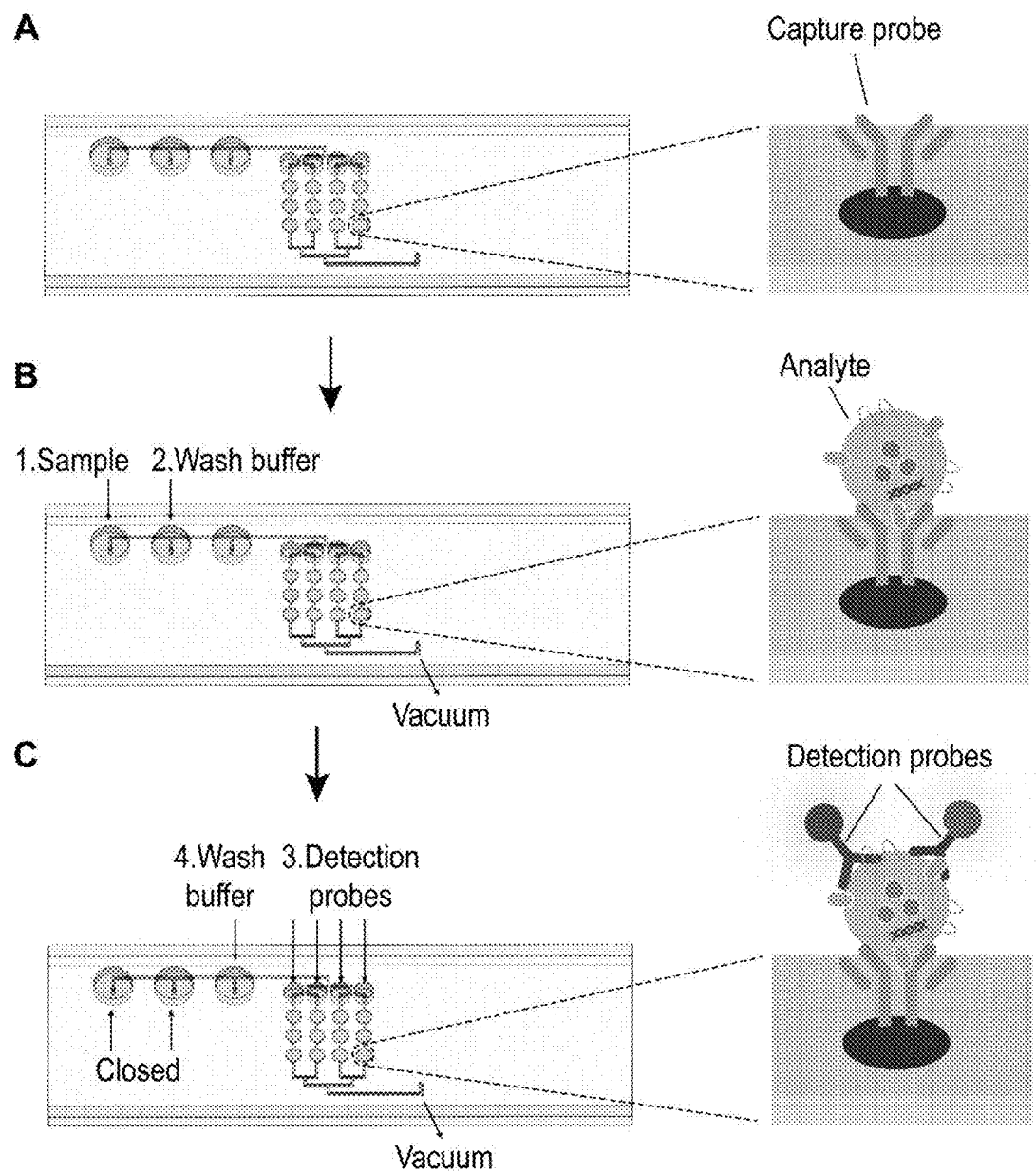
FIG. 7 shows the working mechanism and process of the detection under control.

FIG. 7 described the working mechanism of an exemplary device and the process undergone in the reaction chamber during detection.

In some embodiments, the analyte-capturing agent, which is a capture antibody, is previously immobilized in the substrate layer 5 as shown in FIG. 7A. On each circular detection region, capture probes (e.g., antibodies or oligonucleotides) are immobilized on the glass slides in advance. In some embodiments, the conjugation is achieved via the reaction of amino groups on capture probes and epoxy group on glass slide to form epoxy-amino covalent bond.

To start the detection process, the sample solution stored in sample reservoir 11 is flowed to reaction zone 34 via sample zone 31. The analyte in the sample solution will be captured on the surface of substrate layer 5. Subsequently the washing buffer solution stored in washing buffer reservoir 12 is flowed to reaction zone 34 via washing buffer zone 32 to wash the reaction chamber. The waste is flowed to waste reservoir 14 under vacuum suction. As shown in FIG. 7B, under the control of pressure control module, the sample with analyte is first injected into the circular detection regions from sample reservoir with an incubation of 15-30 minutes, followed by the injection of wash buffer to remove the uncaptured substance. In this way, the targeting molecules are captured by the capture probes in the detection region.

Then the sample reservoir 11 is closed, and the detection probe is introduced to reaction zone 34 from detection probe reservoir 13 via detection probe zone 33 to produce a detectable signal. The unreacted detection probe solution is washed away by an additional washing step. FIG. 7C shows that 4 different fluorescent detection probes (e.g., antibodies or oligonucleotides) are injected into the reaction chamber from 4 different inlets with an incubation of 30-60 minutes, followed by the injection of another wash buffer to remove the unbounded detection probes. In this way, the analytes are labeled with fluorescent detection probes, which are ready for detection.

Microfluidic Detection System

In another aspect, the present disclose provides a microfluidic device comprising: a microfluidic device, a pressure control module, and a signal detection module.

In some embodiments, the pressure control module comprises a vacuum unit providing negative pressure; and a valve controlling the pressure within the sample reservoir 11, washing buffer reservoir 12, and detection probe reservoir 13. In some embodiments, the negative pressure drives the liquid flow within the microfluidic device.

In some embodiments, the signal detection module detects an optical signal generated within the reaction chamber.

In some embodiments, the microfluidic detection system further comprises a sealing layer between the microfluidic device and the pressure control module.

Pressure Control Module

Figure 8:
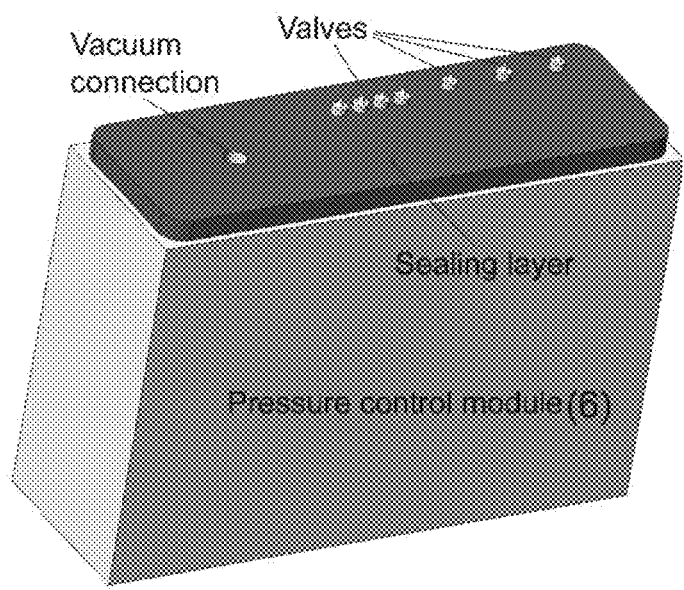
FIG. 8 shows the design of a pressure control module for the operation of the microfluidic device, which comprises a sealing layer, an array of valves, and a vacuum provider.
Figure 9:
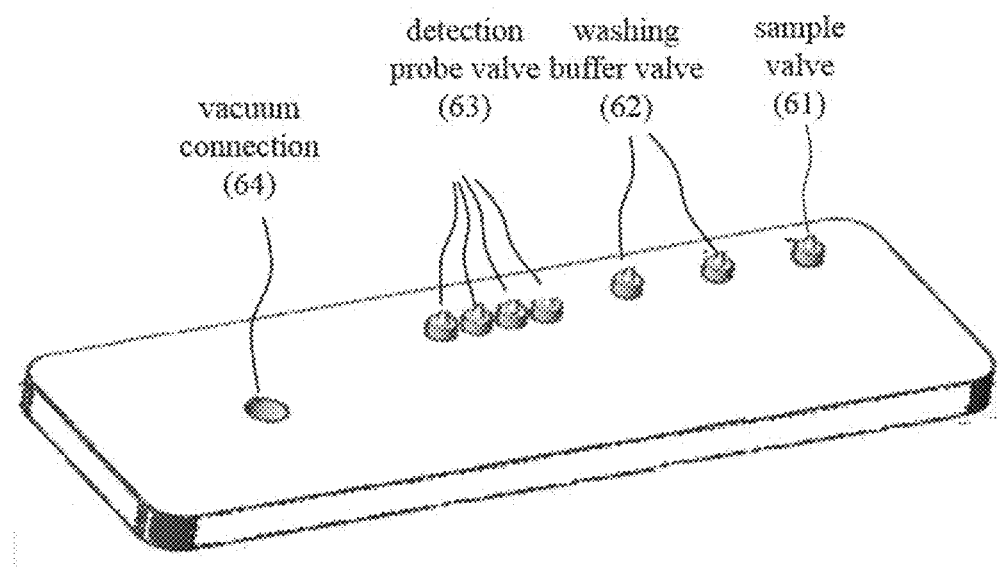
FIG. 9 shows the valves and vacuum channel of the pressure control module.

As shown in FIG. 8 and FIG. 9, the pressure control module comprises a vacuum unit providing negative pressure; and a valve controlling the pressure.

During the operation, the sealing layer attaches onto the top of the reagent layer 1 on the device, with the valves 61 62 63 and vacuum 64 connections aligned to the reagent reservoirs 11 12 13 and waste reservoir 14, respectively.

The vacuum connection 64 is in connected with vacuum access channel 15 in the microfluidic device to provide negative pressure to drive the flow within the microfluidic device.

Figure 10:
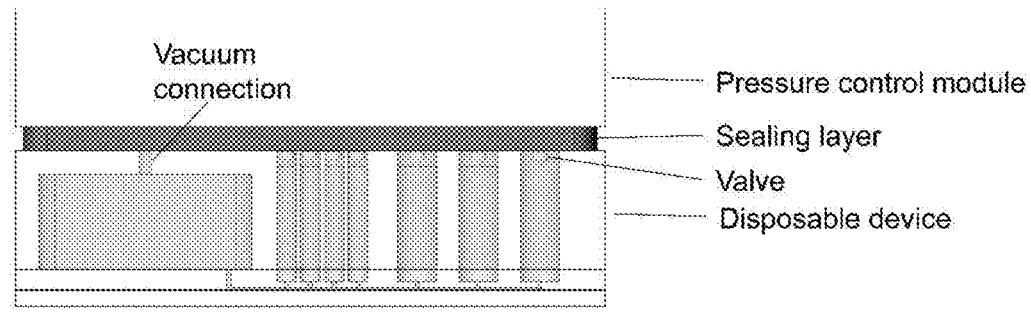
FIG. 10 shows the assembling of the pressure control module and the microfluidic device.

FIG. 10 provides the schematic diagram of the assembly of pressure control module and the microfluidic device.

In some embodiments, the pressure control module further comprises a puncture unit which can puncture the pierceable isolation layer 2. In some embodiments, the puncture unit is integrated into the valve.

Figure 11:
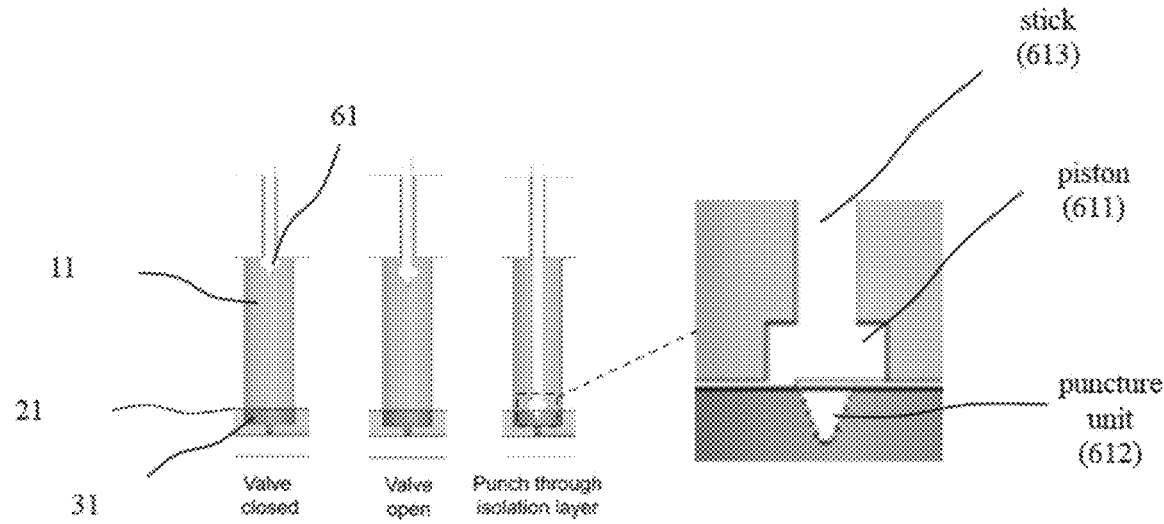
FIG. 11 shows the integration of puncture unit with the valve.

An example for integration of puncture unit with the valve is shown in FIG. 11. In this example, there is a movable stick 613 with a piston 611 and a sharp tip (i.e. puncture unit 612) on each valve, which is used to control the status of the valve 61 (closed or open). Moreover, the stick 613 can puncture through the thin isolation layer 2 with its sharp tip 612 at specific timing, allowing the sample or reagents go into the microfluidic channel under the driven of negative pressure from vacuum. The pressure control module is controlled by a programmable microcontroller to automatically control the valves and vacuum to operate the disposable microfluidic device for analyte detection.

Signal Detection Module

The present disclosure further provides the signal detection module to detect the signal within reaction chamber. In some embodiments, the signal detection module detects an optical signal.

In some embodiment, the signal detection module detects fluorescence.

In some embodiment, the signal detection module is a laser-induced confocal fluorescence scanner or a fluorescence microscope.

In some embodiment, for the purpose of optical signal detection, some layers of the microfluidic device are transparent.

Figure 12:
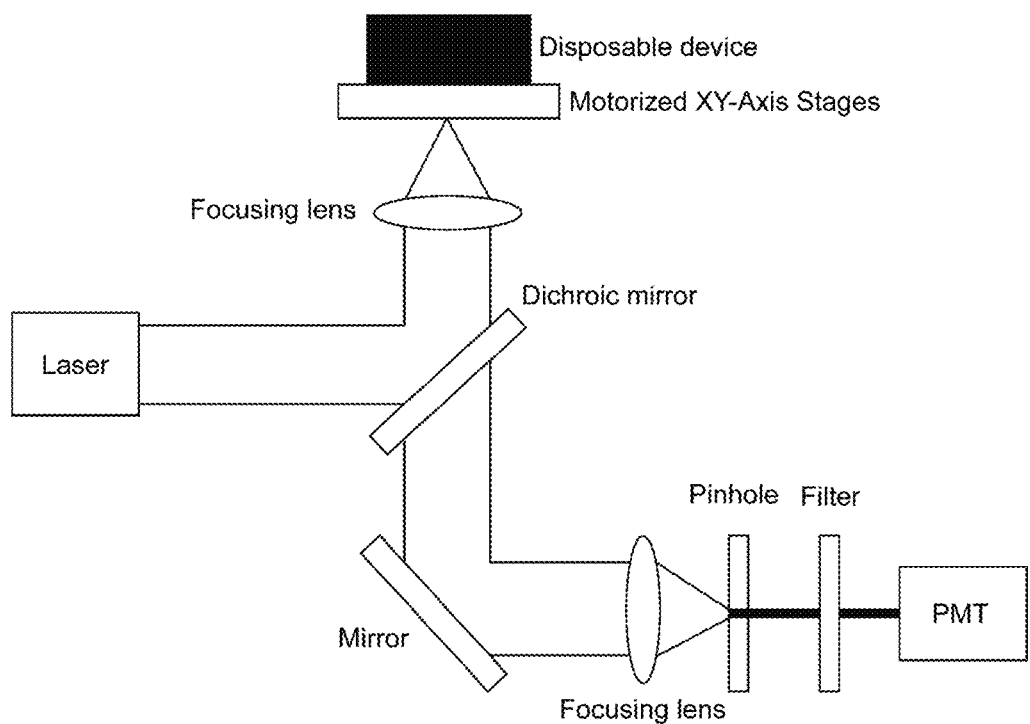
FIG. 12 shows the schematic of the fluorescence detection module.

FIG. 12 shows the schematic of the exemplary fluorescence detection module, comprising a laser source with different excitation wavelengths, various optical components (i.e., lens, mirror, pinhole, filter), a motorized XY-axis stage, and a photomultiplier tube (PMT) to detect emission optical signals. The excitation light with specific wavelength generated by a laser source is directed and focused onto a certain spot of the detection region in the microfluidic device. The fluorescence dye in the detection is excited and emitted a light signal that can be directed to the PMT for intensity measurement. The disposable microfluidic device is placed on the motorized XY-axis stage, that can move along the X-Y plane, allowing for the detection of the whole detection region.

Method for Use

In another aspect, the present disclosure provides a method for using the microfluidic device described herein for detection, which comprises the following steps:
(1) driving the sample solution in the sample reservoir 11 flowing into the reaction zone 34;
(2) driving the detection probe solution in the detection probe reservoir 13 flowing into the reaction zone 34;
(3) allowing the sample solution and the detection probe solution to be mixed in, or to be successively pass through the reaction zone 34 to produce a detectable signal;
optionally, step (1) further comprising puncturing the pierceable isolation layer 21 between the sample zone 31 and the sample reservoir 11;
optionally, step (2) further comprising puncturing the pierceable isolation 23 layer between the detection probe zone 33 and the detection probe reservoir 13.

In some embodiments, the method further comprises a detection step, comprising detecting the signal produced in the reaction step by a signal detection module.

In some embodiments, the method further comprising a washing step, comprising puncturing the pierceable isolation layer between the washing buffer zone and the washing buffer reservoir, and allowing the washing buffer solution to flow into the reaction zone.

It should be understood that there may be multiple washing steps, according to the specific detection methods.

In some embodiments, the sample solution comprises a circulating extracellular vesicle (EV). Antigens commonly present on the surface of circulating EVs are known in the art, such as NMDAR2A, CD9, CD18, CD63, CD81, CD56 and CD171. In some embodiments, the circulating EV is derived from a neuron, and the surface antigen of the circulating EV is NMDAR2A, CD56, or CD171.

In some embodiments, the analyte-capturing agent is a capture antibody against a disease-specific antigen present on the surface of the circulating EV.

In some embodiments, the detection probe is a detection antibody with a detectable label.

In some embodiments, the method is used for the diagnosis of a disease.

In some embodiments, the disease to be diagnosed is Alzheimer's disease. Accordingly, the disease-specific antigen is an AD biomarker, such as a biomarker selected from the group consisting of t-tau, p-tau181, p-tau217, p-tau231, Aβ40, and Aβ42. In one example, the detection antibody is an anti-t-Tau antibody, and the capture antibody is an anti-CD81 antibody.

In some embodiments, the detection antibody is an antibody against a disease-specific antigen present on the surface of the circulating EV.

In some embodiments, the disease-specific antigen is selected from the group consisting of t-tau, p-tau181, p-tau217, p-tau231, Aβ40, and Aβ42.

In some embodiments, the sample is from a subject suspected to have Alzheimer's disease (AD).

In some embodiments, the disease to be diagnosed is tumor or cancer. Accordingly, the disease-specific antigen is a tumor or cancer biomarker, such as a biomarker selected from the group consisting of CA 15-3, CA 125, CEA, HER2, EGFR, PSMA, EpCAM, and VEGF.

In some embodiments, the detectable label is a fluorophore or a fluorescent microsphere. In some embodiments, the detectable label is detected through the signal detection module. In some embodiments, the signal detection module is a laser-induced confocal fluorescence scanner or a fluorescence microscope. It is also understood that the emission spectrum of the detectable label linked to the control antibody should be different from that of the detection antibody, thus the source of the signals could be distinguished. In some embodiments, the detectable label is a fluorophore. In some embodiments, a fluorophore conjugated by the control antibody is Cy5, and a fluorophore conjugated by the control antibody is Cy3, or vice versa.

In yet another aspect, the present disclosure provides a method for treating disease in a subject. In some embodiments, the method comprises administering to the subject a therapeutically effective amount of a drug useful for treating the disease, wherein the subject has been determined to have the disease by the diagnosing method disclosed herein.

Example

Detecting Neuron-Derived Extracellular Vesicles (nEV) Using the Device

Neuron-derived extracellular vesicles (nEV) are considered a significant mediator in regulating AD pathogenesis and are involved in AD propagation. Molecules carried by EVs, including proteins, nucleic acids, and lipids, provide a rich source for profiling AD-associated biomarkers. Moreover, EVs can pass through the blood-brain barrier into the peripheral circulation, enabling interrogation of blood-based AD biomarkers in a less invasive manner. Studies have revealed that circulating EVs in plasma carry substantial amounts of AD biomarkers, such as total tau (t-tau), phosphorylated tau (p-tau), amyloid beta 40 (Aβ40), and amyloid beta 42 (Aβ42), which were observed elevated in AD patients up to 10 years prior to clinical onset. Therefore, rapid and precise profiling the AD biomarkers on EVs provides a non-invasive method for AD diagnostics.

Figure 13:
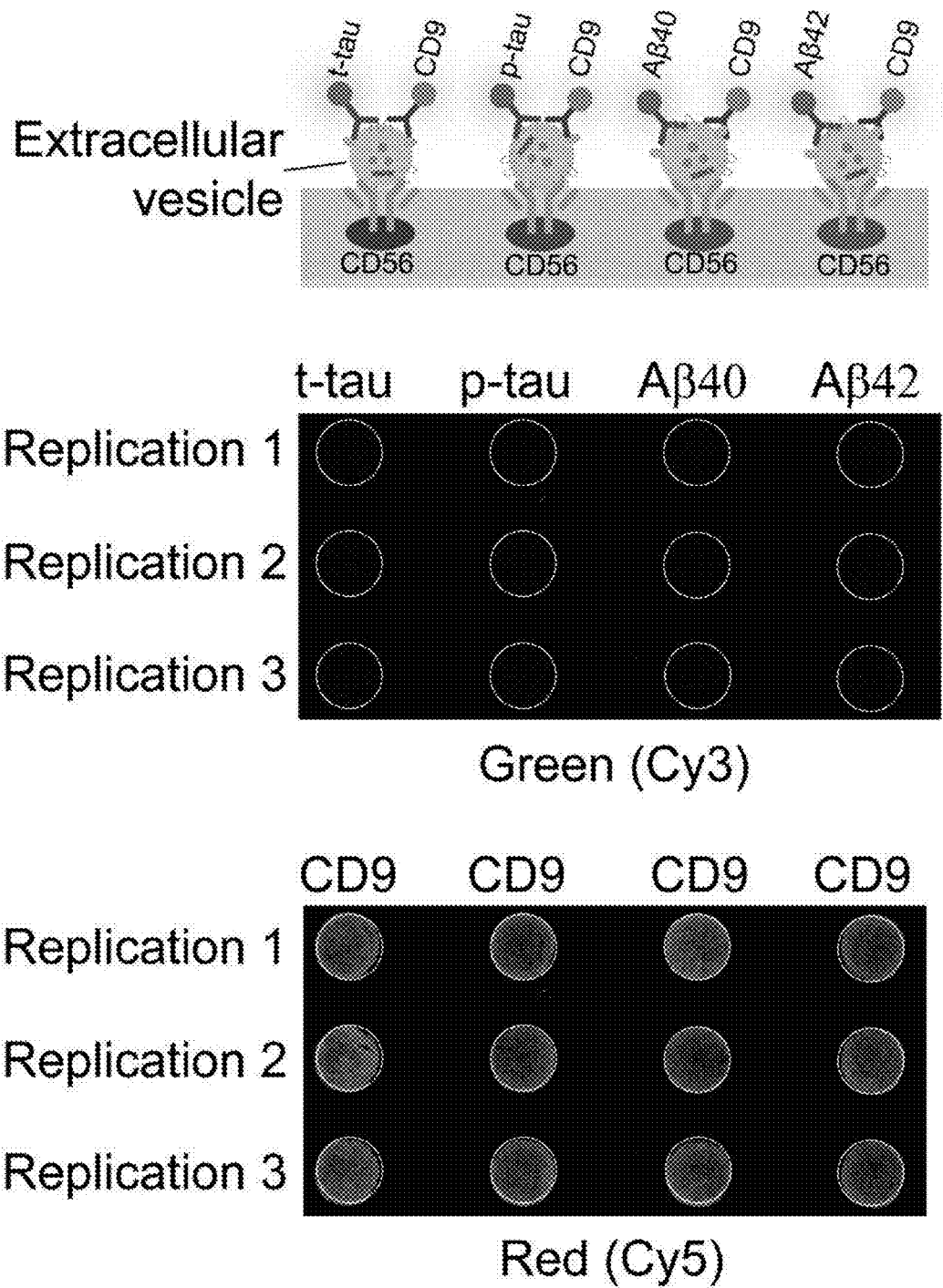
FIG. 13 shows an example of the application of this device.

FIG. 13 shows an example of the application of this device, in which five surface proteins on plasma extracellular vesicles (EV) (i.e., t-Tau, p-Tau, Aβ40, Aβ42, and CD9) were detected for Alzheimer's disease diagnostics. In this case, CD56 antibody (neural cell adhesion molecule, NCAM) was used as capture probes in all detection regions to capture the neuron-cell derived EVs from human plasma. Then four combinations of fluorescent antibodies, targeting t-tau/CD9, p-tau/CD9, Aβ40/CD9, and Aβ42/CD9, were used as detection probes for multiplex detection of AD biomarkers. CD9, labeled with Cy5 fluorescence dye (red), is a common biomarker for extracellular vesicles existing on most EVs and can be used as an internal control for normalization of AD biomarkers. The four AD related biomarkers were labeled with Cy3 fluorescence dye (green). Therefore, for each sample, the device can automatically detect four AD biomarkers and one internal control (CD9) simultaneously within 1 hour for 3 replications, offering a novel approach for Alzheimer's disease diagnosis.

Figure 14:
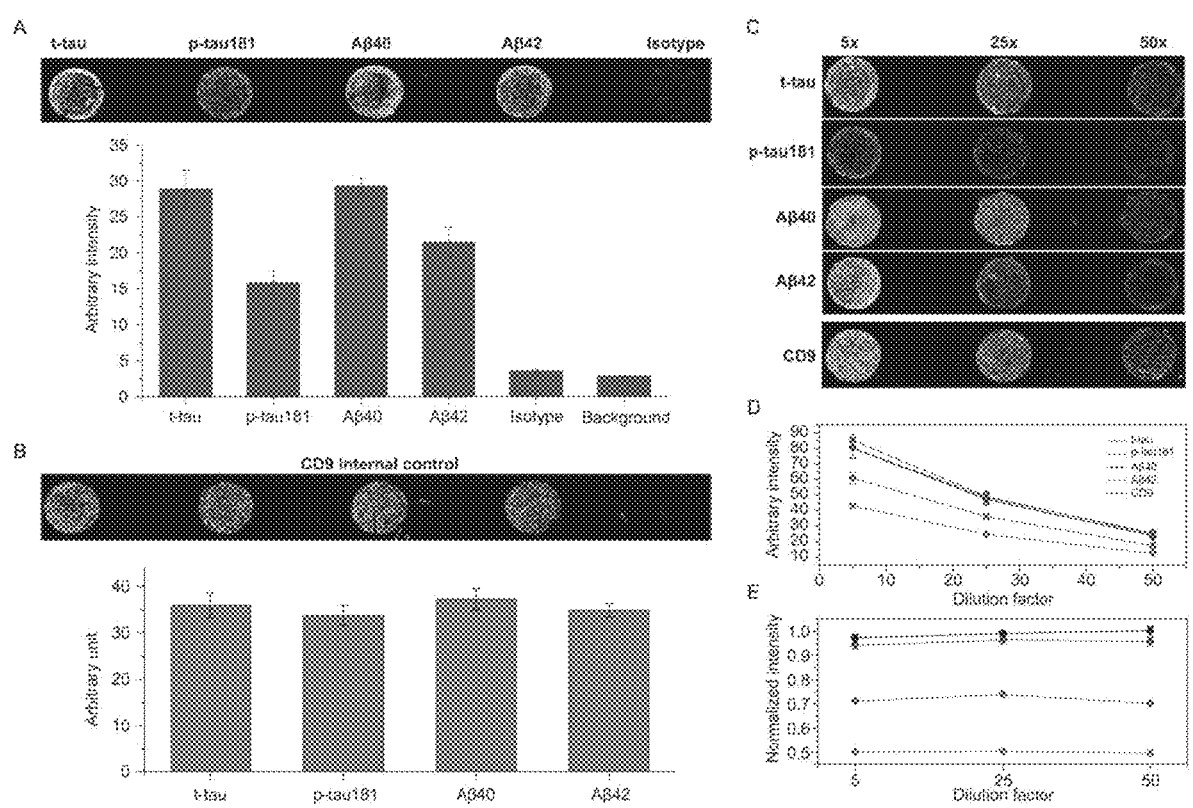
FIG. 14 shows the characterization of the microfluidic system.

FIG. 14A shows the result of detecting AD biomarkers from plasma EV. FIG. 14B shows the result of detecting CD9 internal control from plasma EV. FIG. 14C and FIG. 14D shows the characterization of the signal intensity of AD biomarkers and CD9 of EVs from serial diluted plasma samples (5 to 50 folds). FIG. 14E shows the signal intensity of each AD biomarker after normalization by CD9, indicating that the performance of the microfluidic system in diagnose AD will not affected by the sample dilution. The results demonstrated that the device is promising for diagnosis of Alzheimer's disease, as well as other applicable diseases.

The previous description provides exemplary embodiments only, and is not intended to limit the scope, applicability, or configuration of the disclosure. Rather, the previous description of the exemplary embodiments will provide those skilled in the art with an enabling description for implementing one or more exemplary embodiments. It is understood that various changes may be made in the function and arrangement of elements without departing from the spirit and scope of the invention. Several embodiments were described herein, and while various features are ascribed to different embodiments, it should be appreciated that the features described with respect to one embodiment may be incorporated within other embodiments as well. By the same token, however, no single feature or features of any described embodiment should be considered essential to every embodiment of the invention, as other embodiments of the invention may omit such features.

Specific details are given in the previous description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have also included additional steps or operations not discussed or included in a figure.

Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Furthermore, embodiments may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

While detailed descriptions of one or more embodiments have been give above, various alternatives, modifications, and equivalents will be apparent to those skilled in the art without varying from the spirit of the invention. Moreover, except where clearly inappropriate or otherwise expressly noted, it should be assumed that the features, devices, and/or components of different embodiments may be substituted and/or combined. Thus, the above description should not be taken as limiting the scope of the invention. Lastly, one or more elements of one or more embodiments may be combined with one or more elements of one or more other embodiments without departing from the scope of the invention.

What is claimed is:

1. A microfluidic device comprising:
   (a) a reagent layer, said reagent layer comprising:
   a sample reservoir for loading a sample solution,
   a washing buffer reservoir for depositing a washing buffer solution,
   a detection probe reservoir for depositing a detection probe solution, and
   a waste reservoir for collecting a waste liquid;
   (b) a microfluidic layer beneath the reagent layer, said microfluidic layer comprising:
   a sample zone for receiving a first liquid from the sample reservoir,
   a washing buffer zone for receiving a second liquid from the washing buffer reservoir,
   a detection probe zone for receiving a third liquid from the detection probe reservoir, and
   at least one reaction zone,
   wherein the at least one reaction zone is connected with and allow an inflow of the first liquid from the sample zone, the second liquid from the washing buffer zone and the third liquid from the detection probe zone, and
   wherein the at least one reaction zone is connected with and allow an outflow of the waste liquid from the at least one reaction zone to the waste reservoir;
   (c) a pierceable isolation layer spaced between the reagent layer and the microfluidic layer, wherein the pierceable isolation layer blocks the first, second and third liquid flow from the sample reservoir, the washing buffer reservoir, and the detection probe reservoir to the sample zone, the washing buffer zone, and the detection probe zone, respectively; and
   (d) a substrate layer beneath the microfluidic layer.

2. The microfluidic device of claim 1, wherein the waste reservoir further comprises a vacuum access channel.

3. The microfluidic device of claim 2, wherein the vacuum access channel is connected to a vacuum pump for microfluidic control.

4. The microfluidic device of claim 1, wherein the pierceable isolation layer can be pierced to allow the liquid flow from the sample reservoir, the washing buffer reservoir, and the detection probe reservoir to the sample zone, the washing buffer zone, and the detection probe zone, respectively.

5. The microfluidic device of claim 1, wherein the pierceable isolation layer is adhesive.

6. The microfluidic device of claim 1, wherein the first liquid from the sample zone, the second liquid from washing buffer zone and the third liquid from detection probe zone flow to the at least one reaction zone independently through individual channels.

7. The microfluidic device of claim 1, wherein the sample zone, the washing buffer zone and the detection probe zone are interconnected such that the first liquid from the sample zone, the second liquid from the washing buffer zone and the the third liquid from detection probe zone flow to the at least one reaction zone in a sequence.

8. The microfluidic device of claim 1, further comprising an adhesive layer spaced between the microfluidic layer and the substrate layer.

9. The microfluidic device of claim 8, wherein the adhesive layer does not block the outflow of the waste liquid from the at least one reaction zone to the waste reservoir.

10. The microfluidic device of claim 1, wherein the substrate layer is a glass substrate.

11. The microfluidic device of claim 1, wherein the substrate layer is immobilized with an analyte-capturing agent to form a modified surface.

12. The microfluidic device of claim 11, wherein the modified surface in the substrate layer and the at least one reaction zone in the microfluidic layer jointly form a reaction chamber.

13. The microfluidic device of claim 12, wherein the sample solution and the detection probe solution are mixed in, or successively pass through the reaction chamber to produce a detectable signal.

14. The microfluidic device of claim 11, wherein the analyte-capturing agent is a capture antibody.

15. The microfluidic device of claim 14, wherein the capture antibody is configured to specifically capture an antigen selected from the group consisting of t-tau, p-tau181, p-tau217, p-tau231, Aβ40, Aβ42, NMDAR2A CD9, CD18, CD63, CD81, CD56, and CD171.

16. A microfluidic detection system comprising:
    (a) a microfluidic device of claim 1;
    (b) a pressure control module;
    (c) a signal detection module.

17. The microfluidic detection system of claim 16, wherein the pressure control module comprises:
    (a) a vacuum pup providing a negative pressure, wherein the vacuum pump is connected to a vacuum access channel in the waste reservoir of the microfluidic device;
    (b) a valve controlling the pressure within the sample reservoir, washing buffer reservoir, or detection probe reservoir, wherein the valve is placed on the top of sample reservoir, washing buffer reservoir, or detection probe reservoir.

18. The microfluidic detection system of claim 17, wherein the pressure control module further comprises a puncture unit capable of puncturing the pierceable isolation layer.

19. The microfluidic detection system of claim 18, wherein the puncture unit is integrated into the valve.

20. The microfluidic detection system of claim 16, which further comprises a sealing layer between the microfluidic device and the pressure control module.

21. The microfluidic detection system of claim 16, wherein the signal detection module detects an optical signal with the at least one reaction zone of the microfluidic device.

22. The microfluidic detection system of claim 21, wherein the signal detection module detects fluorescence.

23. The microfluidic detection system of claim 22, wherein the signal detection module is a laser-induced confocal fluorescence scanner or a fluorescence microscope.

* * * * *